(12) United States Patent
Heese

(10) Patent No.: US 10,245,448 B2
(45) Date of Patent: Apr. 2, 2019

(54) PARTICLE BEAM MONITORING SYSTEMS AND METHODS

(71) Applicant: Varian Medical Systems Particle Therapy GmbH., Troisdorf (DE)

(72) Inventor: Juergen Heese, North Rhine-Westphalia (DE)

(73) Assignee: Varian Medical Systems Particle Therapy GmbH, Troisdorf (DE)

( * ) Notice: Subject to any disclaimer, the term of this patent is extended or adjusted under 35 U.S.C. 154(b) by 0 days.

(21) Appl. No.: 15/657,010

(22) Filed: Jul. 21, 2017

(65) Prior Publication Data

US 2019/0022417 A1   Jan. 24, 2019

(51) Int. Cl.
*A61N 5/10* (2006.01)
*G01T 1/02* (2006.01)

(52) U.S. Cl.
CPC ......... *A61N 5/1071* (2013.01); *A61N 5/1077* (2013.01); *G01T 1/02* (2013.01)

(58) Field of Classification Search
CPC ....... A61N 5/1071; A61N 5/1077; G01T 1/02
See application file for complete search history.

(56) References Cited

U.S. PATENT DOCUMENTS 5,834,787 A * 11/1998 Bunker ................ H01J 37/244
                                                      250/397
6,580,084 B1   6/2003 Hiramoto et al.
6,888,832 B2   5/2005 Richardson et al.
(Continued)

FOREIGN PATENT DOCUMENTS

EP   2108401 A1   11/2008
EP   2810693 A2   10/2014
(Continued)

OTHER PUBLICATIONS

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

(Continued)

*Primary Examiner* — Marcus H Taningco

(57) ABSTRACT

Presented systems and methods facilitate efficient and effective monitoring of particle beams. In some embodiments, a system comprises a primary particle beam generator that generates a primary particle beam, and a monitoring component that monitors the primary particle beam. The monitoring component comprises: a reaction component that is impacted by the primary particle beam, wherein results of an impact include creation of secondary photons; a detection component that detects a characteristic of the secondary photons; and a primary particle beam characteristic determination component that determines a characteristic of the primary particle beam based upon the characteristic of the secondary photons. The characteristic of the primary particle beam can include a radiation dose measurement and dose rate. The reaction component can include a foil component. A resolution time of less than a nano second can be associated with detecting the secondary photon characteristic.

21 Claims, 7 Drawing Sheets

(56) References Cited

U.S. PATENT DOCUMENTS

| | | | |
|---|---|---|---|
| 6,920,202 B1* | 7/2005 | Dinsmore | A61N 5/1048 378/119 |
| 7,423,278 B2 | 9/2008 | Amaldi et al. | |
| 7,554,275 B2 | 6/2009 | Amaldi | |
| 7,778,691 B2 | 8/2010 | Zhang et al. | |
| 8,071,966 B2 | 12/2011 | Kaiser et al. | |
| 8,121,253 B2 | 2/2012 | Nelms | |
| 8,253,121 B2 | 8/2012 | Gnutzmann et al. | |
| 8,405,056 B2 | 3/2013 | Amaldi et al. | |
| 8,406,844 B2 | 3/2013 | Ruchala et al. | |
| 8,618,521 B2 | 12/2013 | Loo et al. | |
| 8,636,636 B2 | 1/2014 | Shukla et al. | |
| 8,644,571 B1 | 2/2014 | Schulte et al. | |
| 8,699,664 B2 | 4/2014 | Otto et al. | |
| 8,798,343 B2 | 8/2014 | Kabus et al. | |
| 8,901,519 B2 | 12/2014 | Schardt et al. | |
| 8,986,186 B2 | 3/2015 | Zhang et al. | |
| 9,018,603 B2 | 4/2015 | Loo et al. | |
| 9,033,859 B2 | 5/2015 | Fieres et al. | |
| 9,149,656 B2 | 10/2015 | Tanabe | |
| 9,636,525 B1 | 5/2017 | Sahadevan | |
| 2002/0057760 A1 | 5/2002 | Carroll et al. | |
| 2006/0193435 A1 | 8/2006 | Hara et al. | |
| 2006/0274061 A1 | 12/2006 | Wang et al. | |
| 2008/0049897 A1 | 2/2008 | Molloy | |
| 2009/0283702 A1 | 11/2009 | Umezawa et al. | |
| 2010/0003770 A1* | 1/2010 | Shibata | H01L 22/12 438/5 |
| 2010/0195793 A1 | 8/2010 | Nelms | |
| 2010/0288945 A1 | 11/2010 | Gnutzmann et al. | |
| 2011/0006214 A1 | 1/2011 | Boenig | |
| 2011/0168903 A1* | 7/2011 | Kyele | G01T 1/2914 250/370.1 |
| 2012/0134470 A1* | 5/2012 | Shibuya | A61N 5/1065 378/65 |
| 2012/0136194 A1 | 5/2012 | Zhang et al. | |
| 2014/0152176 A1 | 6/2014 | Chang | |
| 2014/0265823 A1* | 9/2014 | Boisseau | H01J 47/02 313/545 |
| 2014/0270086 A1 | 9/2014 | Krasnykh | |
| 2015/0011817 A1 | 1/2015 | Feng | |
| 2015/0057484 A1 | 2/2015 | Amaldi | |
| 2015/0094838 A1 | 4/2015 | Mac Laverty | |
| 2015/0117616 A1* | 4/2015 | Ishii | H01J 35/08 378/137 |
| 2015/0306423 A1 | 10/2015 | Bharat et al. | |
| 2016/0193482 A1 | 7/2016 | Fahrig et al. | |
| 2016/0225477 A1 | 8/2016 | Banine et al. | |
| 2016/0287905 A1 | 10/2016 | Liger | |
| 2016/0310764 A1 | 10/2016 | Bharadwaj et al. | |
| 2017/0028220 A1 | 2/2017 | Schulte et al. | |
| 2017/0203125 A1 | 7/2017 | Amato et al. | |
| 2018/0235554 A1 | 8/2018 | Burgett | |

FOREIGN PATENT DOCUMENTS

| | | |
|---|---|---|
| EP | 2805745 | 11/2014 |
| EP | 2979728 | 2/2016 |
| EP | 3043863 A1 | 7/2016 |
| JP | 2014161706 A | 9/2014 |
| JP | 2017098000 A | 6/2017 |
| WO | WO2006005059 | 12/2006 |
| WO | 2009042952 A1 | 4/2009 |
| WO | 2010088442 A1 | 8/2010 |
| WO | 2012135196 A1 | 10/2012 |
| WO | 2013038240 A1 | 3/2013 |
| WO | WO2014139493 | 9/2014 |
| WO | 2015038832 A1 | 3/2015 |
| WO | 2015077881 A1 | 4/2015 |
| WO | 2015153746 A1 | 10/2015 |
| WO | 2016094284 A1 | 6/2016 |
| WO | 2016094284 A9 | 6/2016 |

OTHER PUBLICATIONS

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-64 https://accelconf.web.cern.ch/accelconf/p01/PAPERS/FOAA004.PDF.

Th. Haberer, W. Becher, D. Schardt, G. Kraft "Magnetic scanning system for heavy ion therapy" Nuclear Instruments and Methods in Physics Research Section A: Accelerators, Spectrometers, Detectors and Associated Equipment, NIM, Elsevie, Jun. 10, 1993, vol. 330, Issues 1-2, Jun. 10, 1993, pp. 296-305.

Amaldi, TERA Foundation, Novara, Italy A. Degiovanni, CERN, Geneva, Switzerland Linac 2014. Proton and Carbon Linacs for Hadron Therapy U. http://accelconf.web.cern.ch/AccelConf/LINAC2014/papers/friob02.pdf.

Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: S0167-8140(17)30365-1. doi: 10.1016/j.radonc.2017.05.003. [Epub ahead of print] PubMed PMID: 28545957.

Favaudon V, Caplier L, Monceau V, Pouzoulet F, Sayarath M, Fouillade C, Poupon MF, Brito I, Hupé P, Bourhis J, Hall J, Fontaine JJ, Vozenin MC. Ultrahigh dose-rate FLASH irradiation increases the differential response between normal and tumor tissue in mice. Sci Transl Med. Jul. 16, 2014;6(245):245ra93. doi: 10.1126/scitranslmed.3008973. PubMed PMID: 25031268.

Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics. vol. 98 Issue: 2 pp. E16-E16 Supplement: S Meeting Abstract: P003 Published: Jun. 1, 2017.

M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259.

K. Peach, et al. "Pamela—A Model for an FFAG Based Hadron Therapy Machine", Proceedings of PAC07, Albuquerque, New Mexico, USA.

S. Benedetti, A. Grudiev, and A. Latina Phys. Rev. Accel. Beams 20, 040101—Published Apr. 13, 2017.

Z. Li, et. al., Normal conducting cw transverse crab cavity for producing short pulses in spear3, Proceedings of IPAC2017, Copenhagen, Denmark.

Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, pp. 171501-171501-3, Oct. 2010.

Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].

S. Tantawi, Z. Li, patent pending, Title: "Distributed Coupling and Multi-Frequency Microwave Accelerators", Filed: Jul. 9, 2014, U.S. Appl. No. 62/022,469.

S.Tantawi, M.Nasr, "Designs and High Power Tests of Distributed Coupling Linacs" IFIC, Jun. 13-16, 2017, Valencia, Spainhttps://indico.cem.ch/event/589548/contributions/2615455/attachments/1479738/2294080/Mamdouh_High_Gradient_2017.pdf.

Jensen, Aaron, Jeff Neilson, and Sami Tantawi. "X-band multi-beam klystron design and progress report." Vacuum Electronics Conference (IVEC), 2015 IEEE International. IEEE, 2015.

K. Halbach, "Design of permanent multipole magnets with oriented rare earth cobalt material", Nuclear Instruments and Methods, vol. 169, Issue 1, Feb. 1, 1980, pp. 1-10 [http://www.sciencedirect.com/science/article/pii/0029554X80900944].

J. K. Lim, P. Frigola, G. Travish, J. B. Rosenzweig, S. G. Anderson, W. J. Brown, J. S. Jacob, C. L. Robbins, and A. M. Tremaine,

(56) References Cited

OTHER PUBLICATIONS

"Adjustable, short focal length permanent-magnet quadrupole based electron beam final focus system" Phys. Rev. ST Accel. Beams 8, 072401—Published Jul. 15, 2005.

Sayyed Bijan Jiaa, Mohammad Hadi Hadizadeha, Ali Asghar Mowlavi, Mandy Ebrahimi Loushab "Evaluation of energy deposition and secondary particle production in proton therapy of brain using a slab head phantom" Elsevier , Reports of Practical Oncology & Radiotherapy,vol. 19, Issue 6, Nov.-Dec. 2014, pp. 376-384.

J.Perl, J Shin, J Schümann, B Faddegon and H Paganetti, "TOPAS—An innovative proton Monte Carlo platform for research and clinical applications," Med. Phys. 39:6818-6837, 2012, PMID: 23127075, PMID: 23127075.

Lisa Polster, Jan Schuemann, Ilaria Rinaldi, Lucas Burigo, Aimee Louise McNamara, Robert D Stewart, Andrea Attili, David J. Carlson, Alejandro Carabe-Femadez, Bruce Faddegon, Joseph Perl, and Harald Paganetti, "Extension of TOPAS for the simulation of proton radiation on molecular and cellular endpoints," Phys Med Biol. Jun. 10, 2015;60(13):5053-5070, PMID: 26061583.

Vladimir A. Bashkirov a,n , Robert P. Johnson b , Hartmut F.-W. Sadrozinski b , Reinhard W. Schulte a "Development of proton computed tomography detectors for applications in hadron therapy", NIM Nuclear Instruments and Methods in Physics Research A ( under press a the time of writing proposal) http://www.sciencedirect.com/science/article/pii/S0168900215009274 (abstract), Feb. 11, 2016; 809:120-129;Published online Aug. 8, 2015: 10.1016/j.nima.2015.07.066.

Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-240512012/39 (11)/7140/13, 13 pages.

Vincent Favuadon, Laura Caplier, Virginie Monceau, Frederic Pouzoulet, Mano Sayarath, Charles Fouillade, Marie-France Poupon, Isabel Brito, Philippe Hupe, Jean Bounhis,Janet Hall, Jean-Jacques Fontaine, Marie-Catherine Vozenin, vol. 6 Issue 245 245ra93, www.ScienceTranslationalMedicine.org, UltraHigh dose-rate FLASH irradiation increase4s the differential response between normal and tumor tissue in mice, 9 pages.

Valerie Devillaine, Radiotherapy and radiation biology, Radiotherapy—new treatment methods, Radio-toxicity, radio resistance and pediatric cancers, Photo-sensitization and retinoblastoma, 6 pages.

Radiotherapy "flashes" to reduce side effects, An effect for each mode of administration, Images of tissue sections, Ultra-high dose-rate, Science Translational Medicine, Jul. 16, 2014, 3 pages.

To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye-view as applied to beam orientation selection in intensity-modulated radiation therapy.

U. Amaldi el al., "Cyclinacs: Fast-Cycling Accelerators for Hadrontherapy," Nuclear Inst. and Methods in Physics Research, Mar. 2009.

S. Verdú-Andrés et al., "CABOTO, a high-gradient linac for hadrontherapy," Journal of Radiation Research, 2013, 54, pp. i155-i161.

A. Degiovanni et al., "Design of a Fast-Cycling High-Gradient Rotating Linac for Protontherapy," Proceedings of IPAC2013, Shanghai, China, THPWA008, 2013, pp. 3642-3644.

S. Verdú-Andrés et al., "Feasibility Study of a High-Gradient Linac for Hadrontherapy," Proceedings of IPAC2011, San Sebastián, Spain, WEPS045, 2011, pp. 2589-2591.

H. Paganetti et al., "Proton Beam Radiotherapy—the State of the Art," New Technologies in Radiation Oncology (Medical Radiation Series), Springer Verlag, Heidelberg, ISBN 3-540-00321-5, Oct. 2005, 36 pages.

Schuler, Emil, et al. "Experimental platform for ultra-high does rate Flash irradiation of small animals using a clinical linear accelerator." International Journal of Radiation Oncology*Biology*Physics 97.1 (2017 195-203 (Year: 2017).

\* cited by examiner

600

610

Receiving a primary particle beam.

620

Creating a secondary photon corresponding to the primary particle beam.

630

Sensing a characteristic of the secondary photon.

640

Analyzing a characteristic of the primary particle beam based upon the secondary photon characteristic.

Fig. 6

PARTICLE BEAM MONITORING SYSTEMS AND METHODS

FIELD OF THE INVENTION

The present invention relates to the field of particle beam radiation. In some embodiments, radiation systems and methods include monitoring components that facilitate fast and effective monitoring of particle beams.

BACKGROUND

Particle beam radiation can be utilized in a number of different applications and accurately applying an appropriate amount of radiation can be very important. It is often critical to apply an accurate dose of particle beam radiation in medical therapy applications. Particle beam radiation therapy typically includes directing a beam of particles (e.g., ionizing particles, protons, etc.) at an area of tissue. The particles are usually associated with or include a charge. The particles are typically used to stop the growth or spread of the targeted tissue cells by killing them or degrading their cell division ability. While particle beam radiation is generally considered beneficial, there can be a number of potential side effects. The side effects can include unintended damage to DNA of healthy tissue cells. The effectiveness of particle beam radiation is primarily a function of the dose or amount of charged particles that is applied to cancerous cells while avoiding impacts to healthy cells. The amount of charged particles that are applied to the tissue is typically a function of a dose rate or "current" of charged particles and time the targeted tissue is exposed to the radiation. Faster dose rates usually enable shorter exposure times and that can have a number of benefits, including less opportunity for extraneous events to influence the therapy, increased productivity, and greater convenience to the patient.

Many conventional beam radiation therapy systems utilize ionization chambers (e.g., filled with air, a particular gas, etc.) to monitor the dose and dose rate of the particle beam (e.g., proton beam, electron gamma beam, etc.). The gas inside the ionization chamber is ionized by an externally generated particle beam while ions and electrons are collected by electrodes (e.g., by means of an external voltage applied to the ionization chamber, etc.). Typical drift times of electrons and ions are in the order of microseconds to milli-seconds respectively, and the gas amplification depends on the thickness of the gas layer. These drift times typically limit reaction times and detection tolerances, which in turn can pose problems as the dose rates increase. At high dose rates, recombination effects in the gas volume significantly suppress the signal and the chamber output is not proportional to or linear with the beam current. Thus, the ionization chamber usually can not provide a signal that is accurate and useful for monitoring high dose rates.

Conventional ionization chambers can also have problems with electronic noise in the monitoring devices. Electron charge collection can be influenced by magnetic stray fields and reduced air gap or short distances of beam monitoring components from the magnets. The magnetic stray fields can become a limiting factor in radiotherapy systems utilizing high magnetic fields (such as those using superconducting magnets, etc.). The particle beam (e.g., protons, electrons, etc.) can also be scattered by conventional monitoring components. In conventional ionization chambers a charged particle beam is usually widened due to multiple coulomb scattering when transiting the electrodes and the gas volume of an ionization chamber. Thus, traditional particle beam monitoring approaches can have a number of problems, especially as dose rates increase.

SUMMARY

Presented systems and methods facilitate efficient and effective monitoring of particle beams. In some embodiments, a system comprises a primary particle beam generator that generates a primary particle beam, and a monitoring component that monitors the primary particle beam. The monitoring component comprises: a reaction component that is impacted by the primary particle beam, wherein results of an impact include creation of secondary photons; a detection component that detects a secondary photon characteristic; and a primary particle beam characteristic determination component that determines a primary particle beam characteristic based upon the detected secondary photon characteristic. The primary particle beam characteristic can include a radiation dose measurement and dose rate. The reaction component can include a foil component.

The reaction component can be configured as an external window through which the particle beam exits a radiation system. The reaction component can be configured to balance (consider, weigh, etc.) minimization of energy loss characteristics and maintenance of structural characteristics. The minimization of energy loss characteristics is based upon a comparison of energy of the primary particle beam before penetrating the reaction component and after penetrating the reaction component. In some embodiments, a resolution time of less than a nano second is associated with detecting the secondary photon characteristic. The secondary photons can be a plurality of various rays (e.g., Gamma-Rays, x-rays, etc.). The detection component can include spatial resolution components that determine an interaction point of the primary particle beam on the reaction component. The primary particle beam can be included in a FLASH therapy radiation treatment.

In some embodiments, a particle beam monitoring method comprises: receiving a primary particle beam; impinging the primary particle beam on a reaction component; creating a plurality of secondary photons corresponding to a current of the primary particle beam; sensing a characteristic of a portion of the plurality of secondary photons; and analyzing a characteristic of the primary particle beam based upon the characteristic of the portion of the plurality of secondary photons. A characteristic of the secondary photons can vary in accordance with a relationship (e.g., proportional, etc.). The secondary photons can be emitted from a foil component. In some exemplary implementations, the foil component is configured as an external window through which the particle beam exits a radiation system and the foil component is configured to balance minimization of energy loss characteristics and maintenance of structural characteristics. The detecting of the secondary photons characteristic is resolved in a nano second or less.

BRIEF DESCRIPTION OF THE DRAWINGS

The accompanying drawings together with the description are incorporated in and form a part of this specification. They illustrate exemplary embodiments and explain exemplary principles of the disclosure. They are not intended to limit the present invention to the particular implementations illustrated therein. The drawings are not to scale unless otherwise specifically indicated

FIG. 6 is a block diagram of an exemplary particle beam monitoring method in accordance with some embodiments.

DETAILED DESCRIPTION OF THE INVENTION

Reference will now be made in detail to the preferred embodiments of the invention, examples of which are illustrated in the accompanying drawings. While the invention will be described in conjunction with the various embodiments, it will be understood that they are not intended to limit the invention to the various embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one ordinarily skilled in the art that the present invention may be practiced without these specific details. In other instances, well known methods, procedures, components, and circuits have not been described in detail as not to unnecessarily obscure aspects of the current invention.

Presented systems and methods facilitate efficient and effective monitoring of particle beams. In some embodiments, secondary photons are created based upon characteristics of a primary particle beam. The characteristics of the secondary photons can be quickly detected and analyzed, including correlating characteristics of the secondary photons to characteristics of the primary particle beam. The correlation enables rapid determination of primary particle beam characteristics which in turn can be utilized to facilitate application of ultra high dose rates. In some exemplary implementations, a presented system and method can be utilized to monitor particle beam characteristics (e.g., charge, dose, current, dose rate, position, etc.) in FLASH radiation therapy applications.

Figure 1:
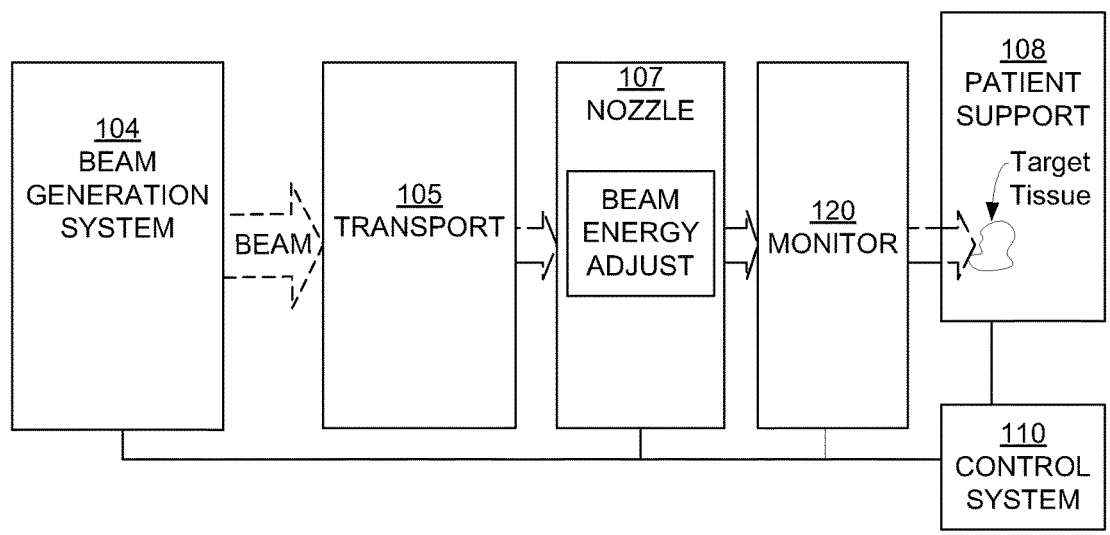
FIG. 1 is a block diagram of an exemplary radiation system in accordance with some embodiments.

FIG. 1 is a block diagram of an exemplary radiation therapy system 100 in accordance with some embodiments. Radiation therapy system 100 includes a beam generation system 104, a beam transport system 105, a nozzle 107, monitor component 120, and control system 110. The beam generation system 104 generates a plurality of particles with a defined energy (e.g., electrons, protons, neutrons, photons, ions, etc.). In some embodiments the plurality of particles are travelling in substantially the same direction. In some exemplary implementations, particles traveling in substantially the same direction are included in a beam. The plurality of particles are then transported to the nozzle by the beam transport system. The beam can be an atom nuclei beam (e.g., from carbon, helium, lithium, etc.).

In some embodiments, the beam generation system 104 includes a particle accelerator. The particle accelerator can include a linear accelerator. The system is compatible with a variety of accelerators (e.g., a continuous wave beam proton accelerator, an isochronous cyclotron, a pulsed proton accelerator, a synchrocyclotron, a synchrotron, etc.). In some embodiments, the accelerator is capable of relatively continuous wave output and extracts particles with a specified energy. This provides a high, continuous wave beam current for the high dose rate per shot or treatment application. A shot is the dose delivered in a relatively short period of time along a line segment through the target tissue. Shots can be included in a scan pattern and independently adjusted (e.g., in intensity, in range, etc.) to irradiate a target tissue volume. The accelerator can be a lower power output cyclotron, such as a cyclotron that accelerates particles to the range of 70-300 MeV. The primary particle beam generator may be configured to correlate the time of the secondary photon emission with the particle beam generation (e.g., to further improve signal-to-noise ratio, primary beam energy measurement, etc.).

The beam transport system 105 can include various components (e.g., dipole magnets, bending magnets, etc.) that direct (e.g., bend, steer, guide, etc.) the beam through the system in a direction toward and into the nozzle 107. The beam generation system 104 and the beam transport system 105 may also include components that are used to adjust the beam energy entering the nozzle 107. In some embodiments, sets of quadrupole magnets are located along the beam paths in the beam transport system 105. In some exemplary implementations, the radiation therapy system may include one or more multileaf collimators (MLCs). A MLC leaf can be independently moved back-and-forth by the control system 110 to dynamically shape an aperture through which the beam can pass. The aperture can block or not block portions of the beam and thereby control beam shape and exposure time.

The nozzle 107 can be used to aim the beam toward various locations within an object (e.g., a patient, target tissue, etc.). The object can be located on the supporting device 108 (e.g., a chair, couch, bench, table, etc.) in a treatment room. The nozzle 107 and monitor 120 may be mounted on or a part of a fixed, rotating or movable gantry (not shown) so that it can be moved relative to the supporting device 108. The supporting device may also be moveable. In some embodiments, the beam generation system 104 and beam transport system 105 can also be completely or partially mounted on or is a part of the gantry. In some other embodiments, the beam generation system is separate from the gantry. In some exemplary implementations, a separate beam generation system is in communication with the gantry.

In some embodiments, control system 110 receives and directs execution of a prescribed treatment plan. In some exemplary implementations, the control system 110 includes a computer system having a processor, memory, and user interface components (e.g. a keyboard, a mouse, a display, etc.). The control system 110 can control parameters of the beam generation system 104, the beam transport system 105, nozzle 107, monitor component 120, and supporting device 108, including parameters such as the energy, intensity, direction, size, and/or shape of the beam. The control system 110 can receive data regarding operation of the system 100 and control the components according to data it receives. The data can be included in the prescribed treatment plan. In some embodiments, the control system 110 receives monitoring information from monitor component 120 and analyzes the performance and treatment being provided by radiation therapy system 100. The monitor component can measure and track particle beam current and particle beam charge which are used to draw a correlation with the dose rate and dose amount respectively. In some embodiments, control system 110 can direct adjustments to the radiation therapy system 100 bases upon the analysis of dose and dose rate.

As noted above, the particle beam entering the nozzle 107 can have a specified energy and the nozzle 107 includes one or more range shifting and modulating components that can affect the energy of the beam. In some embodiments, the nozzle 107 includes components such as magnets that control (e.g., steer, guide, deflect, scan, etc.) the beam particles in "X and Y directions" to scan a target tissue volume. The target tissue volume can be in a patient on the supporting device 108.

In some exemplary implementations, adjustments in the particle beam energy can be used to control: the range of the beam (e.g., the extent that the beam penetrates into target tissue, etc), the dose delivered by the beam, the depth dose curve of the beam, depending on the type of beam. For example, for a proton beam or an ion beam, the beam energy adjuster can control the location of the Bragg peak in the target tissue. The beam energy adjuster can include various components (e.g., range modulator, a range shifter, etc.). The nozzle 107 can also include a beam energy adjuster that affects the energy of the particle beam. The beam generation system 104 and transport system 105 may also include components that are used to adjust the beam energy entering the nozzle 107.

Radiation therapy system 100 can be utilized for high dose rate treatments. Some treatment approaches include ultra-high dose rate treatment or modality referred to as FLASH radiotherapy. Therapeutic windows associated with FLASH therapy often enable reduced normal tissue toxicity while maintaining cancerous tissue tumor control. Monitor component 120 can monitor dose rates and doses typically associated with FLASH therapies, unlike conventional monitoring approaches the usually have a number of difficulties and issues when trying to monitor fast or high dose rates. In some exemplary implementations, the FLASH radiotherapy dose rate can be at least 4 Gray (Gy) in less than one second and as much as 20 Gy or 40 Gy in less than a second. In some exemplary implementations, the FLASH radiotherapy dose rate can be more than 40 Gy in less than one second. The radiation therapy systems and methods are also compatible with multiple field treatment approaches in which different fields are associated with a particular treatment trajectory and a dose per field that is a portion or fraction of a total dose delivery. The multiple field treatment approaches can enable dose delivery for each faction/field to be effectively monitored.

Figure 2:
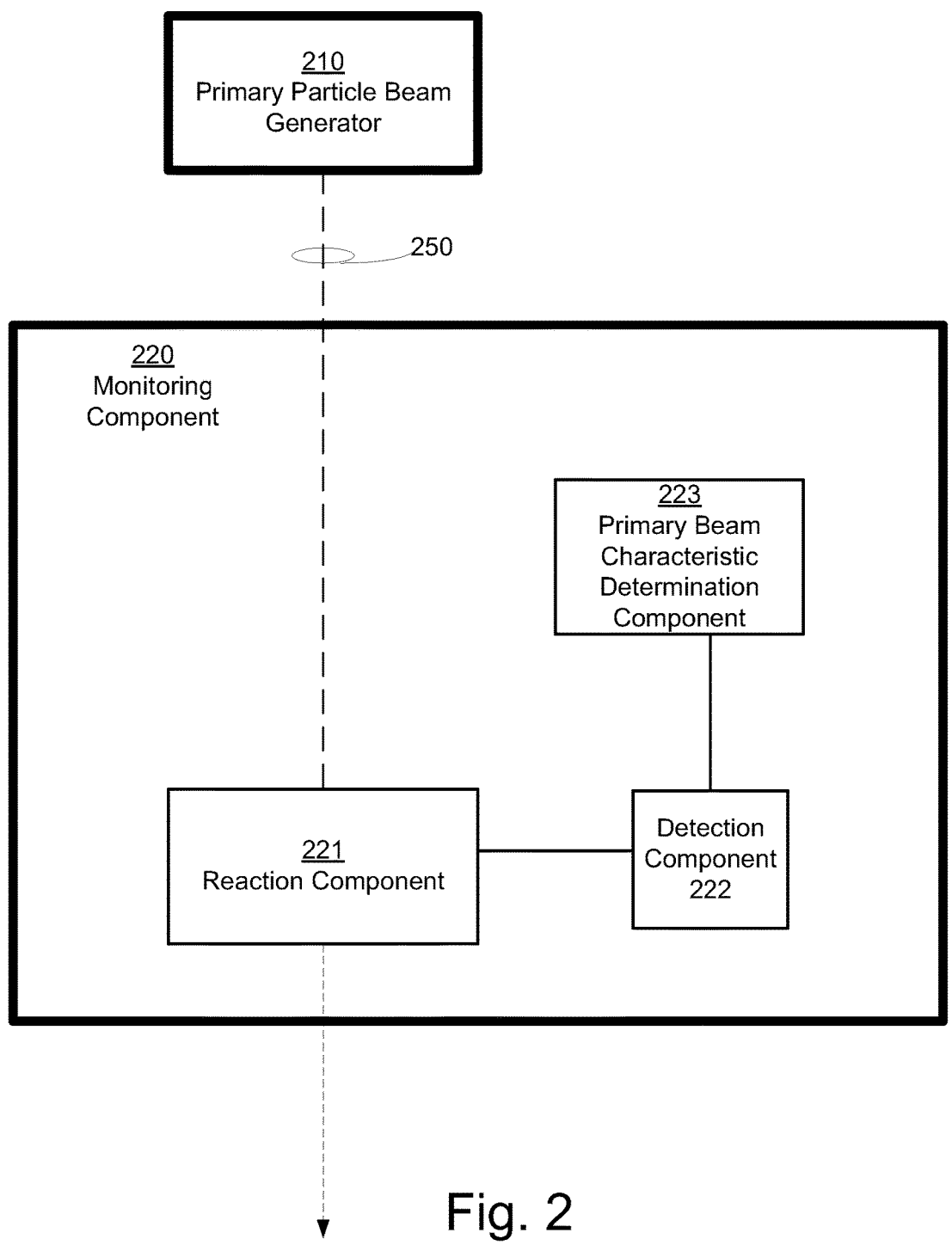
FIG. 2 is a block diagram of another exemplary system in accordance with some embodiments.

FIG. 2 is a block diagram of an exemplary system 200 in accordance with some embodiments. System 200 comprises a primary particle beam generator 210 that generates a particle beam 250, and a monitoring component 220 that monitors the primary particle beam. The monitoring component comprises a reaction component 221, a detection component 222, and a primary particle beam characteristic determination component 223. The reaction component 221 is impacted by characteristics of the particle beam, wherein results of an impact include creation of a plurality of secondary photons. The detection component 222 detects a characteristic of the secondary photons. The primary particle beam characteristic determination component 223 determines a characteristic of the primary particle beam based upon the characteristic of the secondary photons.

In some exemplary implementations, the primary particle beam generator 210 can be similar to beam generation system 104 and nozzle 107, and monitoring component 220 can be similar to monitor component 120. Exemplary system 200 can also include a control component similar to control system 110. In some embodiments, the primary particle beam characteristic determination component 223 can be included in the control system. Primary particle beam characteristic determination component 223 can include a memory configured to store directions or instructions on performing primary particle beam characteristic determination and a processor configured to perform the instructions.

The detection component can include a radiation detector (e.g., scintillation detector, gamma camera, etc.). In some embodiments, the number of secondary photon rays (e.g., x-rays, gamma rays, etc.) is detected and secondary photon ray energy is not necessarily a required detection parameter. In some exemplary implementations, the time resolution of the detector components can be in the pico second to nano second region, and the system is able to handle very high count rates without pile-up. It is appreciated that radiation therapy system 200 can be utilized in monitoring operations for FLASH radiation therapy.

A primary particle beam characteristic determination component can be utilized to perform various different analyses based upon detected secondary photon characteristics. The analysis of the primary particle beam characteristics can include determination of a dose and dose rate. The secondary photon yield or number of detected photon rays per unit time is substantially proportional to the primary particle beam current, which in turn can be converted into dose rates. The number of detected photon rays during beam "on" time can be converted to the dose delivered during a primary particle beam "on" time.

Figure 3:
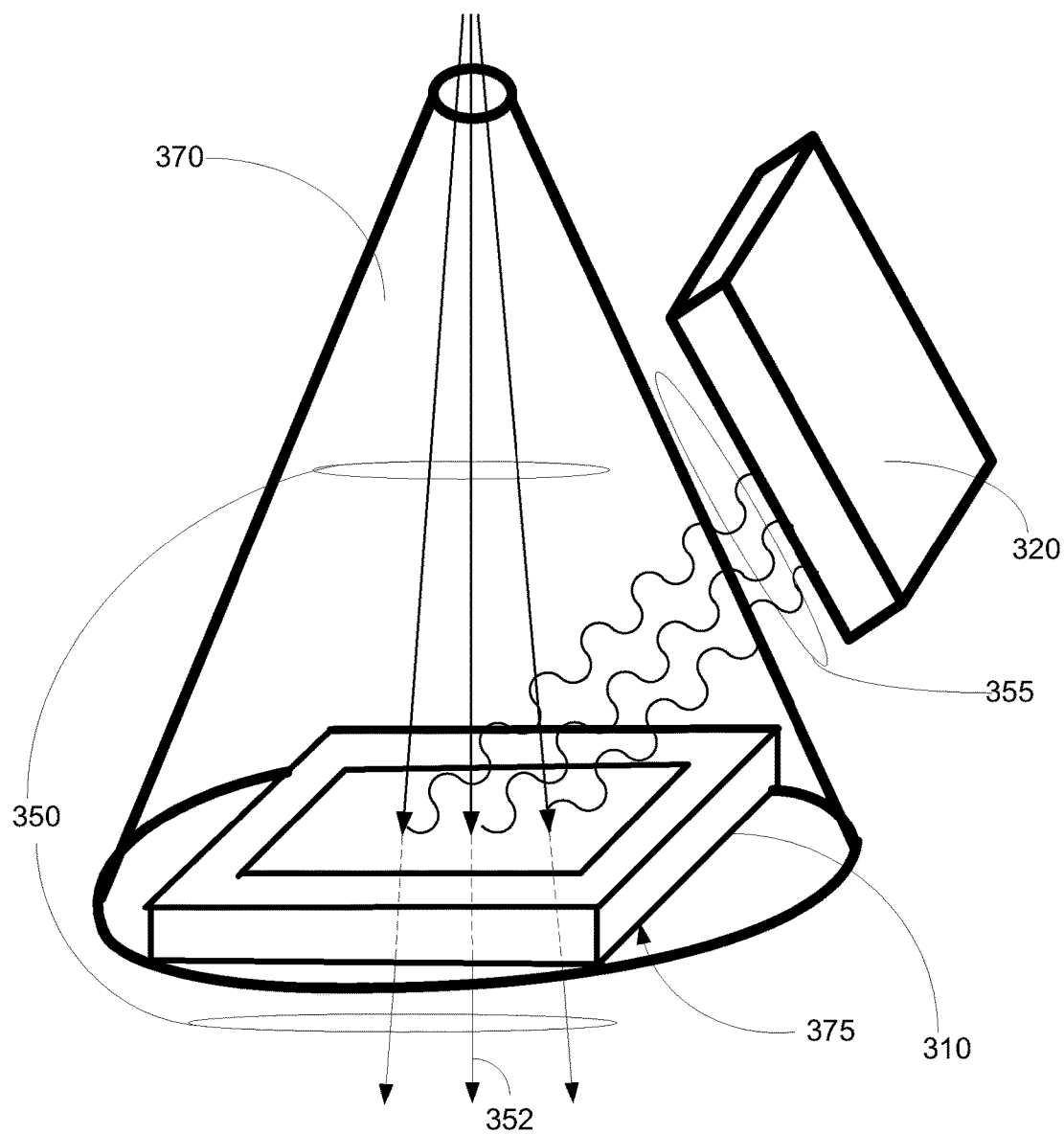
FIG. 3 is a block diagram of an exemplary monitoring system in accordance with some embodiments.

FIG. 3 is a block diagram of an exemplary monitoring system 300 in accordance with some embodiments. Monitoring system 300 includes reaction component 310, and detection component 320. In some embodiments, reaction component 210 and detection component 220 are similar to reaction component 310 and detection component 320. In some exemplary implementations, the reaction component 310 includes a foil component that emits secondary photons 355 when impinged by a primary particle beam 350. In some embodiments, the primary particle beam is relatively homogenous and the secondary photons are emitted isotropically from interaction points in the reaction component 310. The reaction component 310 can include thin foil (e.g., metal, plastic, metal coated plastic, etc.) which can be mounted perpendicular to a primary particle central beam path 352. It is appreciated that a variety of materials can be included in the foil (e.g., Gold, Lead, high Z element, Carbon/Hydrogen compound, polyimide foil, etc.). Monitoring system 300 can include a vacuum region or chamber 370 and atmospheric air pressure 375 can be resisted by reaction component 310. It is appreciated detection component 320 can be configured in various locations (e.g., inside the vacuum chamber, on the wall of the vacuum chamber, outside the vacuum chamber, etc.). Monitoring system 300 can include a primary particle beam characteristic determination component (not shown) similar to particle beam characteristic determination component 223 coupled to detection component 320.

A reaction component can be configured based upon a variety of considerations. The reaction component can be configured so that the primary particle beam can penetrate the reaction component. In some embodiments, a percentage of the primary particle beam energy is lost as the primary particle beam penetrates the reaction component. Characteristics of the reaction component (e.g., material, thickness, etc.) can impact the amount of energy loss (e.g., the thinner the reaction component the smaller the energy loss of the primary beam, etc). In some exemplary implementations, the thickness of the reaction component is configured based upon the amount of energy loss. A thin reaction component is one in which there is a small percentage energy loss associated with penetrating the reaction component as compared to the energy of the primary particle beam received by monitoring device (e.g., less than 1%, 1% to 5%, etc.). In some exemplary implementations, the reaction component is configured to minimize or reduce the energy loss.

In some embodiments, the reaction component forms an area or window in an exterior surface of the monitoring device. The reaction component can be configured to provide structural support characteristics to the monitoring component. The exterior surface can be the last system surface of the radiation system that influences the primary particle beam as it travels towards target tissue. Thus, there are not additional radiation system components that contribute to beam widening due to multiple Coulomb scattering, which in turn enables small or minimum spot sizes of the primary particle beam. In some exemplary implementations, the reaction component is an area in an exterior surface of a monitoring device vacuum chamber and is configured to provide structural support against exterior atmospheric pressure. In some exemplary implementations, the foil is in the range of tenths of millimeters or below (e.g., 200 μm plus or minus 20%, 10 μm plus or minus 20%, etc.).

It is appreciated that the reaction component can be configured based upon balancing multiple considerations. The reaction component structural characteristics can be balanced against or compared to energy loss characteristics. In some exemplary implementations, a dimension of the reaction component is selected based upon low energy loss characteristics associated with thin dimensions balanced with thick dimension structural integrity characteristics. The thickness of a reaction component can be reduced down to be as thin as possible while still maintaining thickness sufficient enough to maintain structural integrity. The reaction component can be configured with substantially constant thickness so that there are relatively constant reaction cross-sections.

In some embodiments, the secondary photons are included in high energy/high frequency ray (e.g., x-rays, gamma rays, etc.). The rays are created by the primary particle beam impinging on the reaction component. Particle beams impinging on a reaction component of given material can create characteristic x-rays associated with material composites in the reaction component by Coulomb interactions and electron rearrangement. The x-rays can be in the 1 keV to 100 keV range depending on the material. Particle beams impinging on a reaction component of another particular material can create gamma rays that are emitted isotropically from interaction points in the foil. In some exemplary implementations, gamma rays in the MeV range result from nucleus interactions associated with particle beams (e.g., proton beams, ion beams, etc.) of sufficient energy impinging on a reaction component.

A detection component can include spatial resolution features that are position sensitive. In some exemplary implementations, a detection component with spatial resolution is used to determine the interaction point on the reaction component. In some exemplary implementations, the detected emission point of the radiation is the measured beam position that can be converted to the beam position at the isocenter of the device. A detection component can include various components (e.g., a gamma camera, slit camera, etc.).

In some embodiments, a detection component can be position sensitive and sense an indication of the location of the primary particle beam impingement of interaction on the foil. A primary particle beam can move to different interaction points on a reaction component. The locations can correspond to a sequence of images or patterns where the primary particle beam moves to or hits can be created. Confirming compliance that primary particle beam locations or patterns correspond to treatment plans can be helpful to quality assurance and safety (e.g., hit cancerous tissue, avoid healthy tissue, etc.). In some exemplary implementations, a position sensitive detection component has an established geometry to the reaction component and is able to resolve locations of interaction points on the reaction component.

Figure 4:
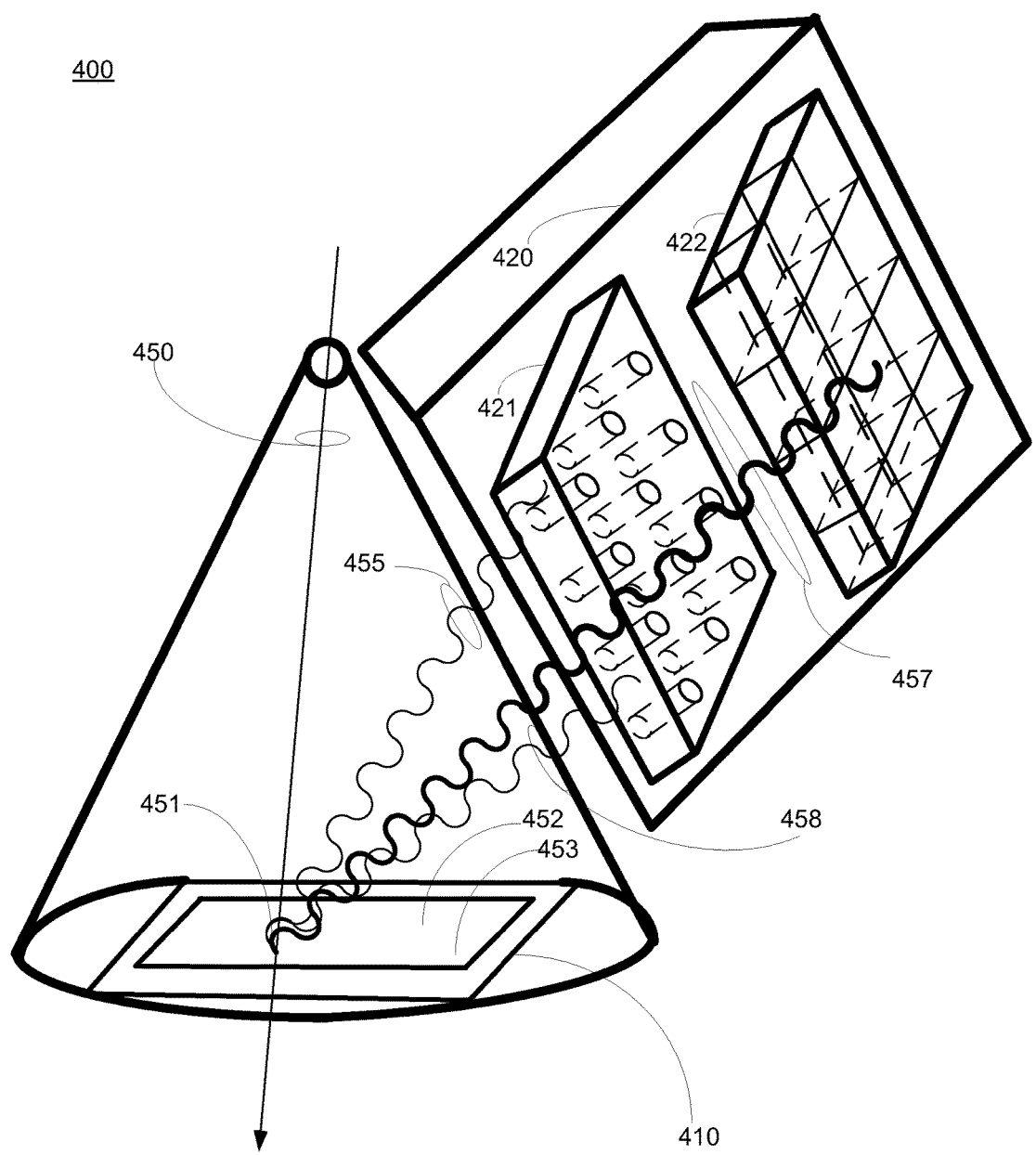
FIG. 4 is a block diagram of an exemplary monitoring system with spatial determination in accordance with some embodiments.

FIG. 4 is a block diagram of an exemplary monitoring system 400 in accordance with some embodiments. Monitoring system 400 includes reaction component 410, and detection component 420. Detection component 420 can include spatial resolution components. In some embodiments, the spatial resolution components can include absorber or collimator 421 and multi-segment position sensitive detection component 422. In some embodiments, the spatial resolution components can include a slit camera that detects the secondary photons and an indication of the primary particle interaction location on a reaction component. It is appreciated the monitoring system 400 can include a primary particle beam characteristic determination component (not shown) similar to particle beam characteristic determination component 223 coupled to detection component 420. In some embodiments, reaction component 210 is similar to reaction component 410, and detection component 220 is similar to detection component 420.

In some exemplary implementations, a relatively narrow or "pencil" primary particle beam 450 hits or impinges reaction component 410 at interaction point 451. Secondary photons 455, 457 and 458 are emitted from an area around interaction point 451 when the primary particle beam 450 interacts with reaction component 410. Secondary photons 457 pass through collimator 421 to multi-segment position sensitive detection component 422. Secondary photons 455 and 458 do not passes through collimator 421 to multi-segment position sensitive detection component 422. Based upon results of the multi-segment position sensitive detection component 422 the position or location of the interaction point 451 can be determined. Primary particle beam 450 can move and hit or impinge reaction component 410 at various interaction points (e.g., 452, 453, etc.). Again, based upon results of the multi-segment position sensitive detection component 422 the position or location of the interaction points (e.g., 452, 453, etc.) can be determined.

In some embodiments, in addition to monitoring dose and dose rates at very small or quick time resolutions, the monitoring system can also monitor the accuracy of the application area rapidly. In some exemplary implementations, the primary particle beam scans an area and the detection component can track the locations of the scanning impingement movement on the reaction component. This information can be used by the radiation system to respond and take fast corrective measures if the primary particle beam location deviates from the prescriptions of the treatment plan.

In some embodiments, an exemplary monitoring system includes a plurality of reaction components and detection components. The exemplary monitoring system can include safety features. The reaction components and detection components can be duplicative or redundant.

Figure 5:
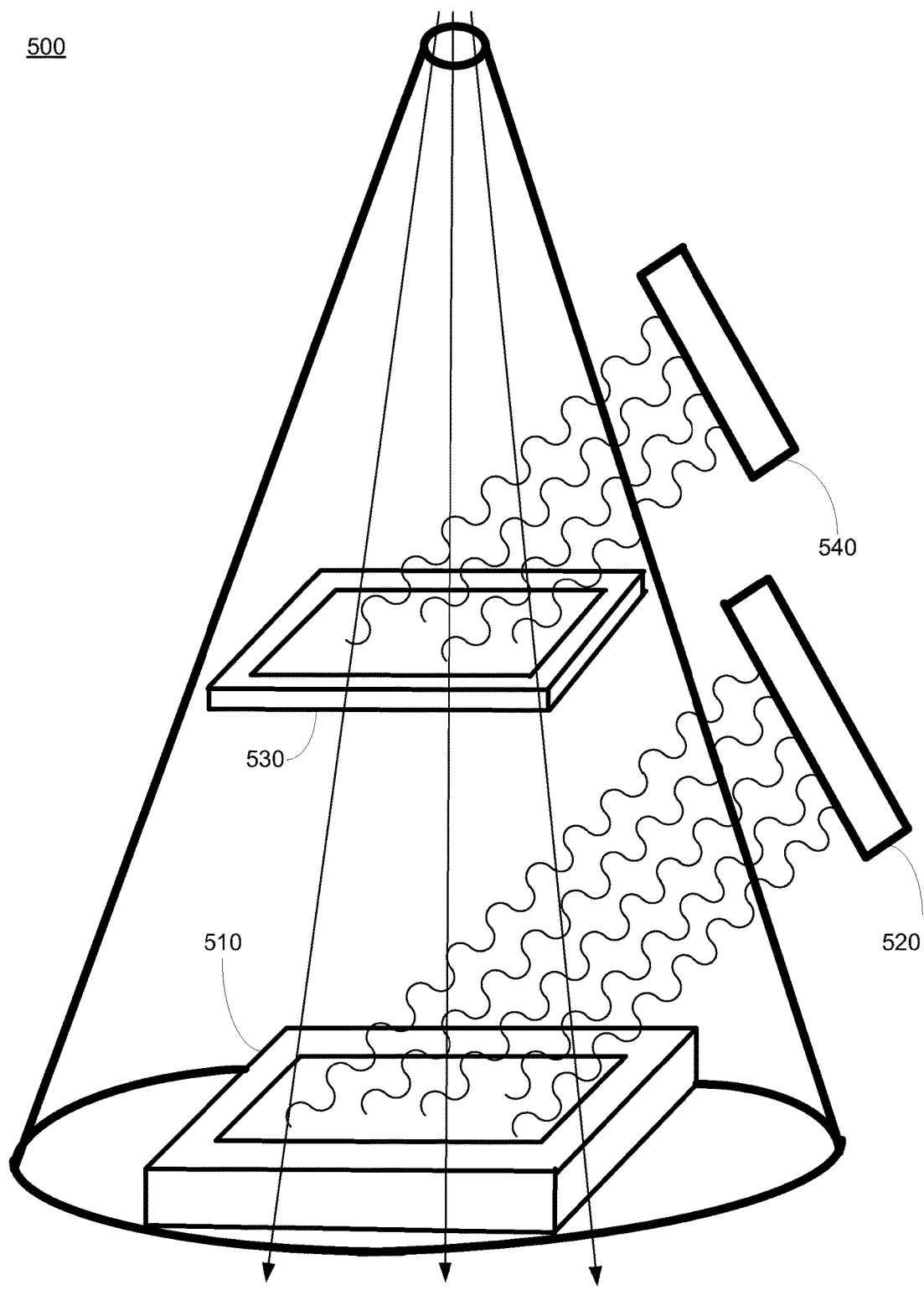
FIG. 5 is a block diagram of another exemplary monitoring system in accordance with some embodiments.

FIG. 5 is a block diagram of an exemplary monitoring system 500 in accordance with some embodiments. Monitoring system 500 includes a plurality of reaction components 510 and 530 and a plurality of detection components 520 and 540. In some embodiments, the reaction component and detection components can be different and facilitate different types monitoring or monitoring with different sensitivity levels. The material included in the reaction component 510 and 530 can be different (e.g., Gold, Lead, Carbon, etc.). The energy of secondary photons emitted from the reaction components and detected by the detection components can be different. In some exemplary implementations, material included in the reaction component 510 and 530 can be different (e.g., Gold, Lead, Carbon, etc.). The reaction components 510 and 530 can emit similar or respectively different photons (e.g., corresponding to x-rays, gamma rays, etc.). The thickness of the foil in respective reaction components 510 and 530 can be different. A top or inner reaction component 510 can be relatively thin (e.g., result in lower absorption, scatter, etc.) and a lower or outer reaction component 530 can be a little thicker (e.g., more structural support, resist external air pressure, etc.). It is appreciated a reaction component and detection component can be included in an ionization chamber and utilized in conjunction with ionization type monitoring.

FIG. 6 is a block diagram of an exemplary particle beam monitoring method 600 in accordance with some embodiments. In some embodiments, particle beam monitoring method enables a detection of a secondary photon characteristic in resolution times of less than a nano second. In some exemplary implementations, particle beam monitoring method 600 can be implemented on system 200.

In step 610, a primary particle beam is received. In some embodiments, a primary particle beam is received from a particle beam generation system.

In step 620, secondary photons are created. In some embodiments, the primary particle beam is impinged on a reaction component and a plurality of secondary photons is emitted from the reaction component in response to the impinging. A characteristic of the secondary photons can vary in accordance with a relationship (e.g., proportional) to a characteristic of the primary particle beam. The secondary photons are emitted from a foil component. The foil component can be configured as an external window through which the particle beam exits a radiation system and the foil component is configured to balance minimization of energy loss characteristics and maintenance of structural characteristics.

Figure 7:
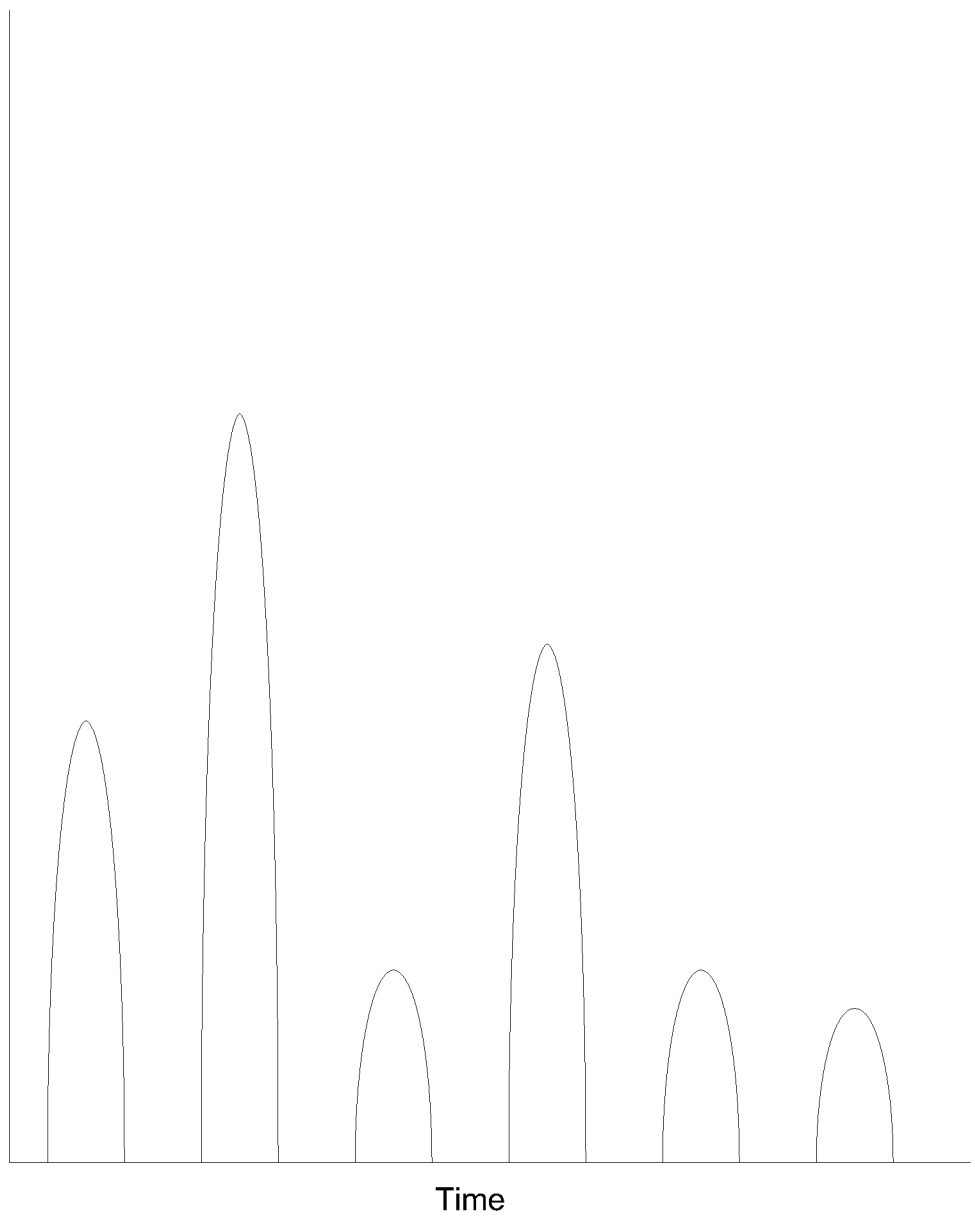
FIG. 7 is a block diagram of an exemplary graph of sensed output signal values over time in accordance with some embodiments.

In step 630, a secondary photon characteristic is sensed. In some exemplary implementations, a characteristic of a portion of the secondary photons is sensed. The emission position of the secondary photons can also be determined. In some embodiments, sensing the characteristic of the portion of the plurality of secondary photons is resolved in a nano second or less. In some exemplary implementations, an x-ray or gamma ray signal is sensed. FIG. 7 is a block diagram of an exemplary graph of sensed output signal values over time in accordance with an embodiment.

In step 640, a characteristic of the primary particle beam is analyzed based upon the secondary photon characteristic. The characteristic of the primary particle beam can include a dose and dose rate.

In some embodiments, a presented monitoring approach utilizes photon detection rather than ionization reactions to extrapolate characteristics of a particle beam. In addition to providing information on dose and dose rates, the monitor information can be fed back or utilized to direct adjustments in the particle beam generation components operations. In some exemplary implementations, the ability to rapidly resolve measurements of particle beam characteristics can be utilized by high resolution dose delivery controls in particle beam generation components. In some embodiments, the monitoring system and method are resistant (e.g., immune, impervious, etc.) to recombination effects and insensitive to magnetic fields. The monitoring system and method can also facilitate noise reduction compared to a typical traditional ionization chamber.

Thus, the presented systems and methods facilitate efficient and effective radiation beam monitoring. In some embodiments, a system can allow dose rate monitoring that is: linear up to ultra high beam currents, provides reaction times in the nano second region sufficient to provide quick reaction times for ultra high dose rate beams, allows dose monitoring by integration of the dose rate, and provide spatial resolution for beam position monitoring of the scanned particle beam. Unlike traditional approaches, in some embodiments there are no or reduced impacts associated with: 1) recombination effects that interfere with monitoring; 2) impacts from magnetic fields due monitoring activities, and 3) signal-to-noise ratio of signal output. In some exemplary implementations, linear monitoring output is maintained for ultra high dose rates and pico amps to nano amp electric currents can be measured.

Some portions of the detailed descriptions are presented in terms of procedures, logic blocks, processing, and other symbolic representations of operations on data bits within a computer memory. These descriptions and representations are the means generally used by those skilled in data processing arts to effectively convey the substance of their work to others skilled in the art. A procedure, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical, or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are associated with the appropriate physical quantities and are merely convenient labels applied to these quantities. Unless specifically stated otherwise as apparent from the following discussions, it is appreciated that throughout the present application, discussions utilizing terms such as "processing", "computing", "calculating", "determining", "displaying" or the like, refer to the action and processes of a computer system, or similar processing device (e.g., an electrical, optical or quantum computing device) that manipulates and transforms data represented as physical (e.g., electronic) quantities. The terms refer to actions and processes of the processing devices that manipulate or transform physical quantities within a computer system's component (e.g., registers, memories, other such information storage, transmission or display devices, etc.) into other data similarly represented as physical quantities within other components.

The foregoing descriptions of some specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as suited to the particular use contemplated. It is intended that the scope of the invention be defined by the Claims appended hereto and their equivalents. The listing of steps within method claims do not imply any particular order to performing the steps, unless explicitly stated in the claim.

What is claimed is:

1. A radiation system comprising:
a primary particle beam generator that generates a primary particle beam; and
a monitoring component that monitors the primary particle beam, wherein the monitoring component comprises:
a reaction component configured as an external window through which the primary particle beam exits the radiation system, wherein the reaction component is impacted by the primary particle beam and results of an impact include creation of secondary photons;
a detection component that detects a secondary photon characteristic; and
a primary particle beam characteristic determination component that determines a primary particle beam characteristic based upon the secondary photon characteristic.

2. The system of claim 1, wherein the primary particle beam characteristic includes a radiation dose measurement.

3. The system of claim 1, wherein the primary particle beam characteristic includes a dose rate.

4. The system of claim 1, wherein the reaction component includes a foil component.

5. The system of claim 1, wherein the primary particle beam exits a radiation system through the reaction component and is forwarded towards target tissue.

6. The system of claim 1, wherein the reaction component is configured to balance minimization of energy loss characteristics and maintenance of structural characteristics.

7. The system of claim 6, wherein the minimization of energy loss characteristics is based upon a comparison of energy of the primary particle beam before penetrating the reaction component and after penetrating the reaction component.

8. The system of claim 1, wherein a resolution time of less than a nano second is associated with detecting the secondary photon characteristic.

9. The system of claim 1, wherein the detection component includes spatial resolution components that determine an interaction point of the primary particle beam on the reaction component.

10. The system of claim 1, wherein the primary particle beam is a FLASH therapy radiation treatment.

11. A particle beam monitoring method comprising:
receiving a primary particle beam;
creating a plurality of secondary photons corresponding to the primary particle beam at a reaction component;
forwarding the primary particle beam from the reaction component towards target tissue;
sensing a characteristic of a portion of the plurality of secondary photons; and
analyzing a characteristic of the primary particle beam based upon the characteristic of the portion of the plurality of secondary photons.

12. The method of claim 11, wherein a characteristic of the plurality of secondary photons varies in accordance with a relationship to a characteristic of the primary particle beam and the relationship is utilized in analyzing the characteristic of the primary particle beam.

13. The method of claim 11, wherein the characteristic of the primary particle beam includes a radiation dose measurement.

14. The method of claim 11, wherein the characteristic of the primary particle beam includes a dose rate.

15. The method of claim 11, wherein the plurality of secondary photons are emitted from a foil component.

16. The method of claim 11, wherein the foil component is configured as an external window through which the primary particle beam exits a radiation system and the foil component is configured to balance minimization of energy loss characteristics and maintenance of structural characteristics.

17. The system of claim 11, wherein the sensing the characteristic of the portion of the plurality of secondary photons is resolved in a nano second or less.

18. A particle beam monitoring device comprising:
a reaction component that forwards a primary particle beam towards target tissue and is affected by characteristics of a primary particle beam, wherein results of an affect include creation of a plurality of secondary photons;
a detection component that detects a characteristic of a portion of the plurality of secondary photons; and
a beam characteristic analysis component that analyzes the results of the reaction.

19. The particle beam monitoring device system of claim 18, wherein the plurality of secondary photons are included in rays.

20. The particle beam monitoring device system of claim 18, wherein the plurality of secondary photons are included in Gamma-Rays.

21. The particle beam monitoring device of claim 18, wherein the plurality of secondary photons are included in X-rays.

* * * * *